United States Patent
Latche et al.

(12)

(10) Patent No.: US 6,376,212 B1
(45) Date of Patent: Apr. 23, 2002

(54) POLYPEPTIDE COMPOUNDS AND NUCLEOTIDE SEQUENCES PROMOTING RESISTANCE TO EUTYPA DIEBACK IN PLANTS

(75) Inventors: Alain Latche, Toulouse; Jean-Paul Roustan, Castanet; Mondher Bouzayen; Jean-Claude Pech, both of Toulouse; Jean Fallot, Auzeville, all of (FR)

(73) Assignee: Societe des Domaines Viticoles Martell, Cognac (FR)

( * ) Notice: Subject to any disclaimer, the term of this patent is extended or adjusted under 35 U.S.C. 154(b) by 0 days.

(21) Appl. No.: 09/432,160

(22) Filed: Nov. 2, 1999

Related U.S. Application Data (62) Division of application No. 09/015,754, filed on Jan. 29, 1998, now Pat. No. 6,063,986.

(30) Foreign Application Priority Data

Jan. 29, 1997 (FR) ............................................ 97 00962

(51) Int. Cl.$^7$ ........................... C12Q 1/26; C12N 15/82; C12N 15/63; C12N 5/14; C07H 21/04
(52) U.S. Cl. ..................... 435/25; 435/468; 435/320.1; 435/410; 536/23.1; 536/24.1; 536/23.6
(58) Field of Search ............................. 536/23.1, 24.1, 536/23.6; 800/295, 278; 435/25, 320.1, 410, 418, 419, 468

(56) References Cited

U.S. PATENT DOCUMENTS 6,063,986 A * 5/2000 Latche et al. ............... 800/279

OTHER PUBLICATIONS

French Search Report, mailed Nov. 7, 1997. (Application 9700962).

Iuchi et al., "Novel Drought–Inducible Genes in the Drought–Tolerant Cowpea: Cloning of cDNAs and Analysis of the Expression of the Corresponding Genes," *Plant & CellPhysiology*, 37:8, p. 1073–1082 (1996).

Deswarte et al., "Transport, Cytoplasmic Accumulation and Mechanism of Action the Toxin Eutypine in Vitis vinifera Cells," *Journal of Plant Physiology*, 149, p. 330–342 (1996).

Deswarte et al., "Protonorphic Activity of Eutypine, a Toxin from Eutypa lata, in Plant Mitochondria," *Archives of Biochemistry and Biophysics*, 334:2, p. 200–205, (1996).

Spencer et al., *Plant Molecular Biology*, 18: 201–210 (1992).

Tey–Ruth et al. "Eutpne, A Phytotoxin produced by Eutypa Lata The Casual Ager of Dying–Arm Disease of Grapevine," *Phytochemistry*, 30:2 p. 471–473 (1991).

Liu et al., *Proc. Natl. Acad. Sci.* 91: 1888–1892 (1994).

\* cited by examiner

*Primary Examiner*—Robert A. Schwartzman
*Assistant Examiner*—Katharine F Davis
(74) *Attorney, Agent, or Firm*—McKenna & Cuneo, LLP (57) ABSTRACT

The subject of the invention is a nucleotide sequence coding for an enzyme with eutypine reductase activity, capable of metabolizing the eutypine synthesized in plants by a fungus of the *Eutypa lata* or *Libertella blepharis* type. The overproduction of eutypine reductase by the plant hose of the fungus enables the consequences of the presence of this fungus in plants to be attenuated or even eradicated.

8 Claims, 3 Drawing Sheets

```
GCAGAATCAACATAATCCACAATGAGCACCGCCGCTGGAAAACTAGTCTGTGTCACCGGC
                         MetSerThrAlaAlaGlyLsyLeuValCysValThrGly
GCTTCCGGTTACATCGCTTCCTGGCTCGTCAAGTTTCTTCTCGAACGCGGCTACACCGTG
AlaSerGlyTyrIleAlaSerTrpLeuValLysPheLeuLeuGluArgGlyTyrThrVal
AAGGCCACCGTTCGCGACACGAATGATCCCAAAAAGGTAGATCACTTGCTCAGCCTTGAT
LysAlaThrValArg AspThr AspAspProLysLysValAspHisLeuLeuSerLeuAsp
GGTGCGAAGGAGAGATTGCATCTCGTGAAGGCGAATCTTCTAGAAGAAGGTTCCTTTGAC
GlyAlaLysGluArgLeuHisLeuValLsyAlaAsnLeuLeuGluGluGlySerPheAsp
TCTGCCGTTGAAGGTGTTCACGCTGTGTTTCACACTGCTTCTCCCTTTTTCAACGATGCC
SerAlaValGluGlyValHisAlaValPheHisThrAlaSerProPhePheAsnAspAla
AAAGATCCGCAGACTGAGTTGTTGGACCCGGCAGTGAAGGGGACTCTGAATGTTCTGAAA
LysAspProGlnThrGluLeuLeuAspProAlaValLysGlyThrLeuAsnValLeuLys
TCGTGTGTGAACTCGCCCACGCTGAAACGCGTCGTTTTAACTTCTTCTATTGCTGCAGTT
SerCysValAsnSerProThrLeuLysArgValValLeuThrSerSerIleAlaAlaVal
GCGTTCAGCGACAGGCCTAAAAACCCTGATGTTGTGGTTGACGAGACTTGGTATTCTGAC
AlaPheSerAspArgProLysAsnProAspValValValAspGluThrTrpTyrSerAsp
CCGGAATACTGTAAGAGAACAGGGTTATGGTATAACCTTTCAAAGACTCTGGCCGAAGAT
ProGluTyrCysLysArgThrGlyLeuTrpTyrAsnLeuSerLysThrLeuAlaGluAsp
GCTGCCTGGAAATTTGCGAAAGAAAACAACATTGACCTGGTTACAATGAACCCAGCATTG
AlaAlaTrpLysPheAlaLysGluAsnAsnIleAspLeuValThrMetAsnProAlaLeu
GTTGTTGGACCTCTCTTGCAACCAGTGCTTAATACTAGCGCTGCTATAGTTTTAGGTTTA
ValValGlyProLeuLeuGlnProValLeuAsnThrSerAlaAlaIleValLeuGlyLeu
GTTAATGGGGCGAAAACATTTAAAAATGCTTCTTTGGGATGGGTCGACGTGAAAGATGTT
ValAsnGlyAlaLysThrPheLysAsnAlaSerLeuGlyTrpValAspValLysAspVal
GCATTGGCCCATATTCTAGGATATGAGAATGCTTCGGCTAATGGAAGATATTTACTAGTT
AlaLeuAlaHisIleLeuAlaTyrGluAsnAlaSerAlaAsnGlyArgTyrLeuLeuVal
GAGAGAGTAGCACACTTTGGAGATGCTGCCAAGATTTTACGAGATTTATACCCAACATTG
GluArgValAlaHisPheGlyAspAlaAlaLysIleLeuArgAspLeuTyrProThrLeu
CAAATTCCAGACAAGTGTGAAGACGATAAGCCATTAGAACCAATATTTCAGGTTTCGAAG
GlnIleProAspLysCysGluAspAspLysProLeuGluProIlePheGlnValSerLys
GAAAAAGCAAAGAGCTTGGGGATTGACTATATTCCTTTGGAAGTGAGCCTCAAGGACACT
GluLysAlaLysSerLeuGlyIleAspTyrIleProLeuGluValSerLeuLysAspThr
GTGGAGAGCTTGAAGGAAAAGAAGTTTCTGAAAGTTTAATGTTACCCTTCAAGAAACGTG
ValGluSerLeuLysGluLysLysPheLeuLysVal
GAAACCTTCTTATGCCTATGCTTGAGGTAAACTTAGTGTTAAATAAATGGAAAGTGATGT
AAGTTCTGTAATAAGTGATTCTTGGACTGGTTTTTTCTGGTGACAAGTTTCAAAAATGAG
TGACCATGGTAGAGTCTGCGTTCCAGATTGTATCCTTGTGATATTGTATTAGTAGAAGAT
GTTTGTTGCAGCTAATGCACCCATTATTATGTTTTTATCAAAAAAAAAAAAAAA
```

…

POLYPEPTIDE COMPOUNDS AND NUCLEOTIDE SEQUENCES PROMOTING RESISTANCE TO EUTYPA DIEBACK IN PLANTS

This application is a divisional application of Ser. No. 09/015,754, filed Jan. 29, 1998, now U.S. Pat. No. 6,063,986, issued May 16, 2000.

The subject of the invention is compounds implicated in resistance to eutypa dieback in plants as well as agents for combatting this disease, for example in the grapevine.

At present eutypa dieback is the most serious disease of the grapevine. In fact, it is present in vineyards throughout the world; it leads to the premature death of many grapevines of the sensitive varieties and there exist no curative agents. The parasite responsible for eutypa dieback of the grapevine is an ascomycete fungus existing in a perfect form *Eutypa lata* (Carter M. V., 1955, Apricot gummosis—a new development J. Dep. Agric. South Aust. 59: 178–184) Tul and C. Tul. Syn; E armeniacae Hansf. and Carter) or an imperfect form *Libertella blepharis* (Samuel G, 1933 "Gummosis" or "Dieback" in apricot trees J. Dep. Agric. South Aust. 36: 979–980) A. L. Smith (syn. Cytosporina sp.).

Eutypa dieback is certainly an ancient disease, even though the pathogenic agent was observed on the grapevine only in 1973 in Australia. In France the disease was identified with certainty by Bolay in 1977 in the region of Languedoc-Roussillon. From 1978, the observations have multiplied in the vineyards of France which show the expansion of eutypa dieback. The reasons for the spread of this dieback disease, which is endemic, have still not been clearly identified to-day; according to certain authors, this progression might be attributable to the modification of certain cultural practices.

The grapevine is not the only perennial ligneous plant which is host to this parasite. In fact, the signs of eutypa dieback have been observed in particular on trees and bushes such as the apricot, black currant, cherry, tamarind, almond, apple . . .

The disease affects the trunk and the "arms" of the grapevine, sites of development of the mycelium, and the herbaceous parts which, however, never harbour the parasite. The ascospores of the fungus, released by the asci of the perithecia situated on the rind of the contaminated grapevines, penetrate via the wounds resulting from pruning into the lumen of the vessels of the xylem, then germinate at several millimeters from the surface of the wound and colonize the xylem, the cambium and the phloem. The installation of the mycelium in the "wood" of the trunk and the arms of the grapevine leads to the formation of an always well-defined, hard and sectorial, brown necrosis, which has an appearance of dry rot, a sign of a preferential degradation of the cellulose of the wood.

The plants affected by eutypa dieback show typical symptoms in the spring. In the most characteristic cases, the branches are emaciated with short internodes; the leaves of small size, often coiled or even deformed, have a slightly chlorotic appearance and sometimes small marginal necroses. The inflorescences seem to develop normally until flowering, but they may then necrose or give bunches of small grapes (fruit drop). The symptoms described often affect one arm but the disease can then spread to all of the grapevine, leading to the death of the latter.

The duration of the slow incubation of the fungus in the trunk and the arms (3 to 10 years) confers on this disease in insidious character. The expression of the symptoms on the herbaceous organs is uncertain depending on the year: a contaminated grapevine does not show symptoms regularly, certainly for reasons related to environmental factors and in particular to climatic conditions. Moreover, the existence of isolates of different aggressivity has been demonstrated, making still more difficult the recognition of the disease.

The destruction of the parasite in the trunk of the grapevines or the reduction of its expression is not possible to-day. In the absence of curative pest control measures, different prophylactic and preventive measures have been recommended to contain the disease. It is recommended, for example, to limit the pressure of the inoculum by removing old grapevines and the arms cut after the pruning operation. Awareness of the conditions of release and germination of the ascospores has led to several recommendations: prune late while taking account of the climatic conditions (dry and calm weather), avoid prunings causing large surface wounds, protect each pruning wound by the manual application of a fungicide to limit the germination of the ascospores. Finally, the affected stains may be restored by the operation of cutting them back severely, which consists of preserving a stem existing below the diseased part of the trunk and of removing the upper part.

It can be seen that eutypa dieback is certainly harmful because the present pest control agents, uniquely prophylactic and preventive, are restrictive, expensive and of limited scope.

The economic impact of this disease is considerable. The surveys conducted in France since 1988 show that the levels of symptoms are variable and depend on the variety of grapevine and, for a given grapevine, depend on the year and the regions, sometimes up to 50% of the grapevines being subjected to the disease. The most sensitive varieties include the Sauvignon blanc, the Cabernet Sauvignon, the Ugni blanc, the Cinsault and the Chein whereas the Merlot and the Sémillon are the most tolerant.

A network of observations based on a rigorous statistical approach set up in the context of a European contract ("Eutypa dieback control" programme No. 8001-CT-91.205) focussed on 85000 grapevines cultivated in 11 wine-growing regions and on 10 varieties of grapevine. It made it possible to show that all the varieties exhibit symptoms of eutypa dieback but to very variable extents: 30 to 80% in certain regions of Greece, 5 to 10% in the Rioja Alta region (Spain, Tempranillo variety) and in Italy (Trebbiano variety) and less than 2%, even 1%, in the wine-growing areas of Portugal.

This disease may also entail a reduction of the expression of the aromatic quality in certain grapevine varieties. In addition, eutypa dieback requires the premature replacement of the dead varieties which causes the rejuvenation of the vineyard, which is detrimental to quality. It should also be noted that the parasitic fungus plays a pioneer role in the installation of parasitic apoplexy (Carignon C., 1991), fungal complex also responsible for a dieback of the grapevine.

This disease also has indirect effects on quality by modifying the planting of the vines in the vineyard because the sensitive varieties are little by little replaced by more tolerant varieties, while however respectively the restrictions of the registered designation of origin. Furthermore, if the harvest volume is maintained in spite of varieties missing to a high extent, the quality of the wines may be affected.

Consequently, it is clear that for the winegrowers wishing to maintain a regular production of quality wines, eutypa dieback is presently the most worrying disease.

The inventors have shown that eutypa dieback is associated with the synthesis of a compound of the family of the lipophilic acids, 4-hydroxy-3-(3-methylbut-3-en-1-ynyl)

benzaldehyde, called eutypine (Tey-Rulh P. et al. Phytochemistry, vol. 30, No. 2, pp. 471–473, 1991) in some tissues of the host harbouring the parasitic fungus. This toxic molecule is synthesized by the parasitic fungus.

In order to control this disease the inventors have been concerned with the structure and physiology of eutypine when it is synthesized in the host by the parasite and have observed in plants and in particular in the plants resistant to eutypa dieback, the synthesis of degradation products of this toxic constituent.

By the expression "plants resistant to eutypa dieback" is meant in the context of the present application, the capacity of the plants contaminated by the parasite responsible to resist the harmful effects induced directly or indirectly by the presence of the parasite.

This type of resistance may also be explained as the capacity of the plants contaminated by the fungus responsible for eutypa dieback to tolerate the presence of this parasite without their development, including their growth and their physiology, being affected to an extent which would entail the dieback of the plants in question.

The inventors have demonstrated a metabolic pathway for eutypine within the plants contaminated by the parasite, resulting in the synthesis of products non-toxic for these plants; as a result, they have suggested agents for conferring on plants sensitive to eutypa dieback properties of resistance or, where appropriate, agents for increasing the resistance capacities already existing in certain plants towards eutypa dieback.

In this connection, the inventors have identified and characterized in particular a polypeptide with enzymatic activity of the reductase type capable of promoting the degradation of the toxic eutypine into non-toxic constituents including a compound called eutypinol.

The inventors have isolated and identified the eutypine reductase enzyme and have succeeded in characterizing the nucleotide sequence coding for this enzyme.

The nucleotide sequence coding for this enzyme thus constitutes a novel means for considering the production of plants resistant to eutypa dieback in conformity with the definition which was given previously of this resistance. For example, the characterization of this nucleotide sequence makes it possible to prepare transgenic plants capable of overproducing eutypine reductase and of increasing the metabolism of the eutypine produced in the host by the parasite.

Hence the subject of the invention is a nucleotide sequence, characterized in that it codes for a polypeptide with eutypine reductase activity, this polypeptide comprising the amino acid sequence represented in FIG. 1 (SEQ ID NO. 3 and NO. 4).

According to a particular embodiment of the invention, this nucleotide sequence is characterized in that it comprises the nucleotide sequence included between the nucleotides 22 and 975 of the nucleotide sequence shown in FIG. 1 (SEQ ID NO. 3 and NO. 4).

As a variant, such a sequence is characterized in that it corresponds to the sequence shown in FIG. 1 (SEQ ID NO. 3 and NO. 4), which is a complementary DNA sequence (cDNA) of the VRER gene coding for the eutypine reductase molecule.

The subject of the present invention is also a nucleotide sequence hybridizing with one of the sequences previously described under highly stringent conditions.

Such highly stringent conditions are the following: placing in contact with a solution containing SSC (2×), 1% SDS for 5 min at 25° C., then twice for 15 min. at 45° C., then in a solution containing SSC (0.2×), 1% SDS twice for 15 min. at 45° C.

Alternatively, the nucleotide sequence of the invention may be defined in that it possesses a sequence homology of more than 75% with the nucleotide sequence included between the nucleotides 22 and 975 of the sequence shown in FIG. 1 (SEQ ID NO. 3 and NO. 4), or with the nucleotide sequence shown in FIG. 1 (SEQ ID NO. 3 and NO. 4).

Preferably, this homology is greater than or equal to 80% and advantageously greater than or equal to 90%.

The nucleotide sequences may advantageously be used in the procedures of genetic engineering to produce the compounds according to the invention.

In this connection, a sequence should advantageously be used which complies with one of the preceding definitions under the control of a homologous or heterologous promoter, and preferably under the control of a promoter suitable for expression in prokaryotic and/or eukaryotic cells.

Preferably, and depending on the level of eutypine reductase activity desired, recourse should be had to a strong promoter for expressing a nucleotide sequence according to the invention. A suitable promoter is for example the strong promoter 35S of the CaMV (EP-B-0131623) permitting expression in plant cells.

Where appropriate, the promoter used is combined with other regulatory sequences such as expression enhancers.

As examples of vectors, mention should be made of the binary vector pGA described by An, G et al., 1988, Binary Vectors, pp 1–19 in Plant Molecular Biology Manual A3 Kluwer Acad. Pub., Dordrecht, The Netherlands.

The application also relates to recombinant prokaryotic or eukaryotic cells, containing a nucleotide sequence complying with one of the definitions given above.

Valuable recombinant cells in the framework of the embodiment of the invention are for example bacterial cells, in particular *E. coli* or *Agrobacterium tumefaciens* cells. They may also be eukaryotic cells and, in particular, plant cells. As examples, recourse should be had to cells of plant seeds or to grapevine cells, in particular when it is desired to implement resistance to eutypa dieback in the grapevine.

Also included in the framework of the invention are a biological tissue or plant producing a polypeptide compound complying with one of the preceding definitions after transformation by a nucleotide sequence according to the invention. Preferably, the recombinant plant is the grapevine.

The invention also relates to seeds obtained from said plants as well as to a process for the production of these plants or these seeds.

Preferably, the cells, tissues and plants transformed in the context of the invention contain the nucleotide sequence integrated stably into their genome. Any suitable transformation procedure may be used, such as electroporation, bombardment with microprojectiles carrying DNA, for example, by means of a particle gun, the co-culture of explants in the presence of *Agrobacterium tumefaciens.*

Such a production process for a plant or a seed expressing a polypeptide compound with eutypine reductase activity is characterized in that it comprises the steps of a) transformation of a plant cell with a nucleotide sequence defined above or a vector defined above under conditions permitting the stable and functional expression of the protein with eutypine reductase activity encoded in the above-mentioned nucleotide sequence;

b) regeneration of plants from the transformed plant cell of step a) to obtain plants expressing the protein with eutypine reductase activity;

c) where appropriate, production of seeds from the modified plants obtained in step b).

The process of the invention may advantageously be implemented to produce plants of the grapevine family, but also to produce plants resistant to eutypa dieback when these plants are naturally sensitive to this disease, for example perennial ligneous plants such as the apricot, black currant, cherry, tamarind, almond or apple.

Moreover, the subject of the invention is the use of the nucleotide sequence such as defined in the preceding pages as selection agent, a detector of the transformation of cells by means of a defined nucleotide sequence whose expression is coupled to that of the sequence used as selection agent. In the context of this application the sequence or part of the sequence of the VRER gene or its cDNA may be used as selection gene for making it possible to identify cells, tissues or plants genetically transformed by a sequence of interest. In this case, the selection gene is transferred with the gene of interest to the cells that it is desired to transform. The sequence of the gene of interest and that of the selection gene are combined so that the integration and/or the expression of the one is linked to the integration and/or the expression of the other. The value of using the sequence of the invention as selection gene or sequence lies in its making it possible in particular to avoid certain problems linked to the dissemination of the genes, a problem encountered with the genes for resistance to antibiotics or herbicides. In the framework of this application, the transformed cells, tissues or plants may be selected by being placed in contact with eutypine or with any substrate capable of being reduced by the eutypine reductase produced by the selection gene.

The selection of the transformed cells, tissues or organisms which have integrated the selection gene with the aid of eutypine or any suitable substrate should be feasible by prior determination of the threshold sensitivity to eutypine of the cell of the tissue or plant considered. This determination should be made by procedures similar to those known for the determination of the sensitivity of a given species or organism to an antibiotic or herbicide.

Hence the subject of the invention is also a recombinant nucleic acid containing a nucleotide sequence according to the invention, used as selection agent in combination with a sequence of interest, said combination making possible the linked integration of the selection marker and the sequence of interest in a defined cell host.

Consequently, the framework of the invention includes a procedure for the detection of cells transformed by a defined sequence of interest comprising:

a) the transformation of the cells with a recombinant nucleic acid comprising the gene of interest and a selection gene comprising a nucleotide sequence coding for a polypeptide with eutypine reductase activity according to the invention, b) the placing of the cells obtained in step a) in contact with a substrate for eutypine reductase, c) the detection of a reduction reaction undergone by the substrate d) where appropriate, the selection of the transformed cells giving rise to this reduction reaction.

Hence the subject of the invention is also a polypeptide compound with eutypine reductase activity, characterized in that it comprises the amino acid sequence described in FIG. 1 (SEQ ID NO. 3 and NO. 4).

According to this definition, the eutypine reductase activity observed is the capacity conferred on the host of the parasite responsible for eutypa dieback or increased by this polypeptide compound to degrade or metabolize eutypine to degradation products non-toxic for the reference host usually sensitive to the toxicity linked to the presence of eutypine.

Etypine or 4-hydroxy-3-(3-methylbut-3-en-1-ynyl) benzaldehyde is a lipophilis weak acid which has been demonstrated to be capable of being degraded to a hydroxylated derivative, 4-hydroxy-3-(3-methylbut-3-en-1-ynyl) benzylic alcohol, called eutypinol in the context of the present application, as a result of an enzymatic reaction for which the constituent NADPH is a specific co-factor when the reaction is performed in vitro.

In an environment permitting it, the polypeptide compound according to the invention is hence capable of carrying out this enzymatic reaction to metabolize eutypine to a non-toxic derivative, in particular to the form of eutypinol.

Where appropriate, the eutypine reductase activity may be observed on other aldehydic substrates.

The polypeptide compound previously described is characterized by the presence in its structure of an amino acid sequence, the sequence of which has been given in FIG. 1 (SEQ ID NO. 3 and NO. 4); if necessary, it may include additional groups the presence and/or nature of which depends for example on the cell host in which it is expressed.

A valuable compound according to the invention is also characterized in that it has a molecular weight of about 36 kDa, calculated from the coding sequence and measured on the purified protein.

According to a particular embodiment of the invention, the polypeptide compound is characterized in that it is encoded in a nucleotide sequence comprising the coding nucleotide sequence included between the nucleotides 22 and 175 (these end nucleotides being included) of the sequence shown in FIG. 1 (SEQ ID NO. 3 and NO. 4).

The subject of the invention also includes compounds modified with respect to the polypeptide compound previously defined. In particular, they may be polypeptide compounds comprising an amino acid sequence derived from the amino acid sequence described in FIG. 1 (SEQ ID NO. 3 and NO. 4), for example by addition, deletion or substitution of at least one amino acid residue contained in this sequence, the compound formed having a eutypine reductase activity according to the definition which is given above.

When the compound of the invention is obtained by deletion of at least one amino acid residue of the sequence of the polypeptide compound previously described, the deletion may extend to the elimination of one or more fragments unnecessary or inessential for the eutypine reductase activity of the compound complying with the definition of FIG. 1 (SEQ ID NO. 3 and NO. 4).

Similarly, when a derivative of the compounds described above is obtained by substitution of certain amino acid residues, they may be replaced by neutral residues or by residues having the same properties or by residues capable of promoting the desired reducing properties.

According to a variant of the embodiment of the invention, the polypeptide compound is characterized in that it is recognized by antibodies obtained against a polypeptide complying with the amino acid sequence shown in FIG. 1 (SEQ ID NO. 3 and NO. 4).

Such antibodies are for example polyclonal antibodies obtained by immunization of an animal, in particular a rabbit, with the polypeptide compound with eutypine reductase activity according to the invention and recovery of the antibodies formed from the rabbit serum.

Also included in the context of the invention is a polypeptide compound characterized in that its amino acid sequence exhibits a sequence homology of at least 50% with the amino acid sequence shown in FIG. 1 (SEQ ID NO. 3 and NO. 4).

By homology is meant the identity of the amino acids compared when the two amino acid sequences are compared or, in the absence of identity, the conservation of the properties of the original amino acid in the substituted amino acid.

Advantageously, the homology previously in question is equal to at least 70%, and preferably equal to at least 80, even 90%, in numbers of amino acid residues, this homology being evaluated by reference to the amino acid sequence shown in FIG. 1 (SEQ ID NO. 3 and NO. 4).

The polypeptide compounds according to the invention may be obtained by any suitable method and in particular may be isolated from plants, for example from the bean Vigna radiata (Mung Bean) or may also be synthesized chemically or prepared by genetic engineering in particular in recombinant cells.

Other plants may also be used to extract the compounds of the invention, such as the grapevine, the potato, the carrot, etc . . .

Other characteristics and advantages will become apparent in the Figures described below, as well as in the examples.

BRIEF DESCRIPTION OF THE DRAWINGS

FIG. 1: This figure (SEQ ID NO.3) represents the nucleotide sequence of the full length cDNA of the VRER gene. This figure (SEQ ID NO.4) also represents the peptide sequence encoded by the cDNA of the VRER gene.

Figure 2:
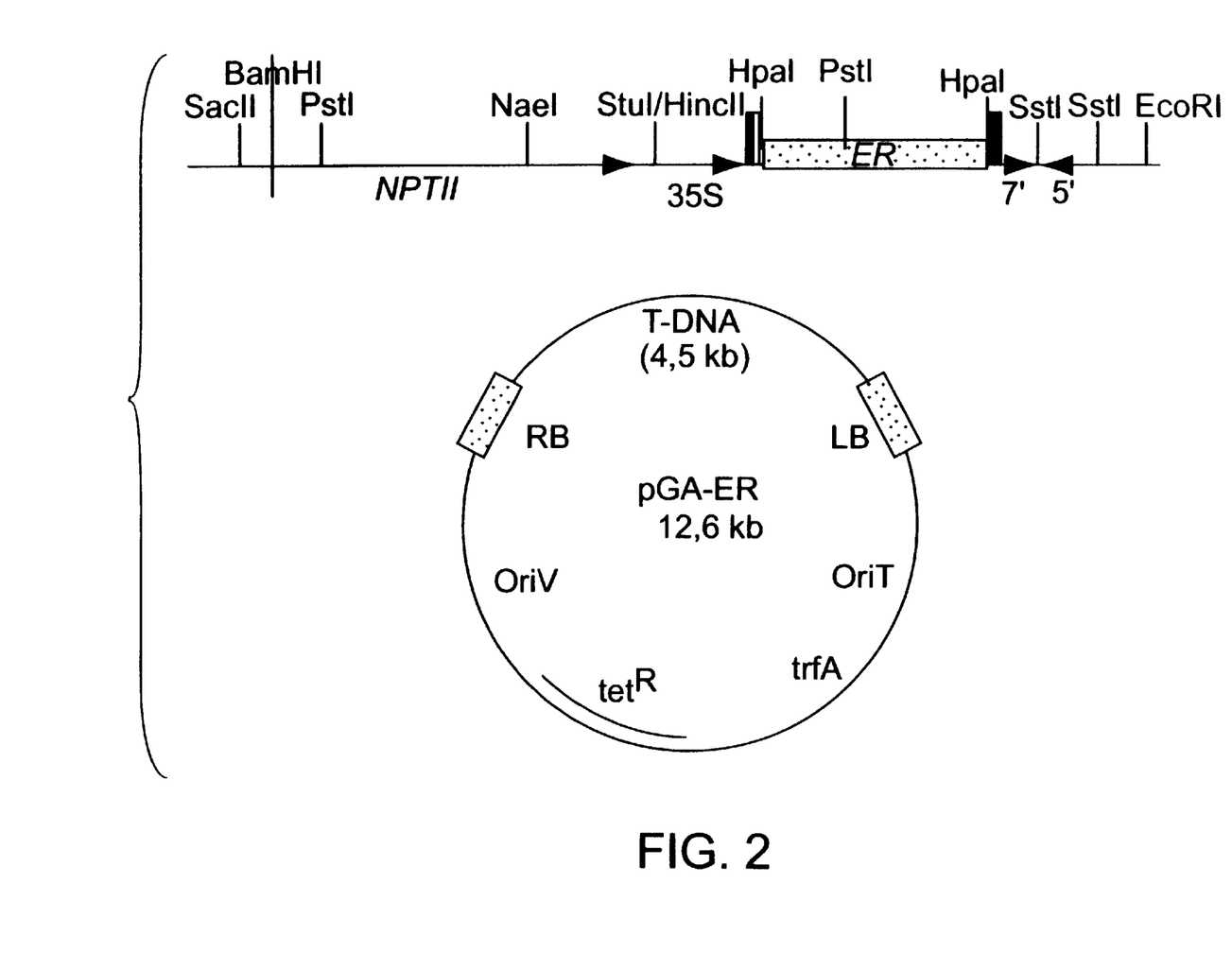
FIG. 2: Schematic representation of the binary vector pGA-ER. RB and LB: right (700 bp) and left (600 cells. These results strongly suggest that eutypine acts a mobile transporter of protons (protonophore).
Figure 3:
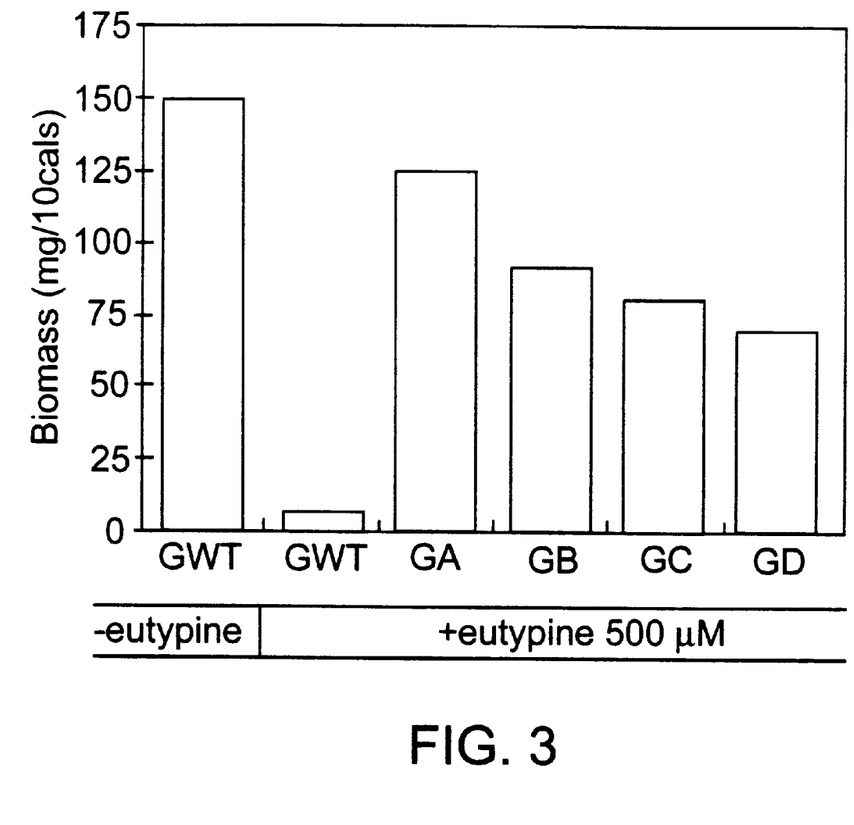

The mode of action of eutypine was confirmed by investigating its effects on the functioning of mitochondria. Eutypine acts as a decoupling agent of oxidative phosphorylation. The complete decoupling of the mitochondria is attained at concentrations of eutypine close to 150 μM. The decoupling effect of eutypine is due to a protonophore effect linked to the dissociable alcohol function of the molecule since a structural analogue which bears a methyl function in the place of the dissociable function has only a very weak effect on the functioning of the mitochondria.

All of these data demonstrate that eutypine acts as a mobile transporter of protons. The protonophore activity of eutypine may, on its own, account for the physiological adverse effects caused by the toxic molecule.

Metabolism of eutypine in grapevine cells

Grapevine cells, placed in the presence of eutypine ($C^{14}$), produce a radioactive compound identified by mass spectrometry. It is a hydroxylated derivative of eutypine, 4-hydroxy-3-(3-methylbut-3-en-1-ynyl) benzylic alcohol, called eutypinol.

This compound does not show toxicity to the grapevine, even at high concentrations, because it does not possess protonophore activity (Table I).

TABLE I

Effect of eutypinol on the viability of protoplasts obtained from leaves of vitroplants of *Vitis vinifera* cv. Cabernet Sauvignon

| Treatment | Viability after 48 hours |
| --- | --- |
| Control | 88 |
| Eutypine | |
| 100 μM | 67 |
| 200 μM | 0 |
| Eutypinol | |
| 200 μM | 86 |
| 500 μM | 83 |

The protoplasts ($4.5 \times 10^5$/ml) are cultured in the presence of eutypine or eutypinol for 48 hours.

In order to demonstrate a relationship between the capacity to metabolize eutypine by the grapevine tissues and the behaviour of the different varieties of grapevine towards eutypa dieback, the detoxification activities of the protoplasts of leaves of the grapevine varieties Ugni blanc (very sensitive), Cabernet Sauvignon (sensitive) and Merlot (tolerant) were compared (Table II).

TABLE II

Degradation of eutypine by protoplasts of different varieties of *Vitis vinifera*

| Varieties | Sensitivity to eutypa dieback in vineyard | Detoxification activity (pmol/min/$10^5$ cells) |
| --- | --- | --- |
| Ugni blanc | very sensitive | 7.9 |
| Cabernet Sauvignon | sensitive | 10.1 |
| Merlot | tolerant | 13.6 |

The protoplasts ($10^6$/ml) obtained from leaves of vitroplants are incubated for 1 hour at 30° C. in the presence of eutypine (100 μM; 0.4 kBq). Then, the phenylacetylenic compounds are extracted, separated by thin layer chromatography and the metabolic rate of eutypine is calculated after determination of the radioactivity associated with eutypine and eutypinol.

It is evident that the protoplasts of the varieties used in the experiments can convert eutypine into eutypinol. The variety Merlot, considered to be tolerant to eutypa dieback in the grapevineyard, possesses a detoxification activity very much greater than that of Ugni blanc, a variety very sensitive to the disease. Furthermore, the detoxification activity of the variety Cabernet Sauvignon, a variety which is also sensitive, is less than that of the variety Merlot.

These data clearly show the existence of a relationship between the ability of these varieties to metabolize eutypine and their behaviour in the vineyard with regard to eutypa dieback.

The conversion of eutypine to eutypinol is catalyzed by a non-membrane enzyme, which specifically requires NADPH as co-factor. Its activity is reduced by reductase inhibitors such as disulfiram and parahydroxymercuribenzoic acid, confirming its membership of this group of enzymes. It has been called "eutypine reductase". The reaction scheme is shown below.

eutypine

+ NADPH, H+ $\xrightarrow{\text{eutypine reductase}}$

+ NADP+ eutypinol

II. Investigation of a gene coding for a protein exhibiting a "eutypine reductase" activity in a heterologous system.

The objective was to isolate a gene coding for a protein exhibiting a "eutypine reductase" activity. It is recognized that the overexpresssion of a gene of a given species in this same species often leads to an overall diminution of the expression of the endogenous gene and of the transgene. On the other hand, the overexpression of a heterologous gene (belonging to a species different from that which is transformed) does not cause this phenomenon.

In order to avoid the phenomenon of co-suppression, a search was made among the different species of grapevine for the presence of an enzyme capable of detoxifying eutypine. Among the species studied, *Vigna radiata* (VR) showed the highest capacity to reduce eutypine. The isolation of the protein was thus performed starting from the tissues of this species.

Purification of the ER protein

The protein exhibiting a "eutypine reductase" activity was purified to homogeneity according to the following protocol, then sequenced.

The seeds of Mung Bean (*Vigna radiata* L. R. Wilcz) were soaked overnight in aerated water. The seeds were then rinsed with water and sown on vermiculite. The plantlets were harvested after 4 days of culture at 23° C. and the hypocotyls (2 cm) were cut for the extraction of the enzyme.

Five hundred grams of hypocotyls of Mung Bean were ground in liquid nitrogen in a bead grinder of the Dangoumeau type. One hundred grams of powder obtained were homogenized in 2 volumes of extraction buffer composed of 0.1 M of K-phosphate (pH 8.0), 10% of glycerol (wt/v), 1% of polyvinylpyrrolidone M 40,000, 30 mM Na ascorbate and 5 mM of dithiothreitol (DTT). The homogenate was centrifuged for 20 min at 48,000 g. The supernatant thus obtained was subjected to a double precipitation with ammonium sulfate at 30 and 70% saturation. The pellet obtained from the precipitation with 70% ammonium sulfate was dissolved in a small volume of 0.1 M K-phosphate buffer (pH 8.0) containing 10% of glycerol and 1 mM of DTT. The enzymatic extract was desalted on a column of Sephadex G25 (PD 10, Pharmacia), then purified in 6 successive steps:

hydrophobic interaction chromatography on a column of Phenyl-Sepharose Cl-4B (Pharmacia);

ionic interaction chromatography on a column of hydroxylapatite (Econo-Pac HTP, BioRad);

molecular exclusion chromatography on a column of Superose 12 HR of type FPLC (Pharmacia);

ion exchange chromatography on a MonoQ 5/5 column of FPLC type (Pharmacia);

chromatography by high performance electrophoresis (HPEC) on native gel chromatography by denaturing electrophoresis (SDS-PAGE).

Alternatively, the ER protein could be purified from Mung Bean seeds by applying the following procedure:

Five hundred grams of hypocotyls of Mung Bean were ground in a propeller grinder in the presence of two volumes of extraction buffer composed of 0.1 M of borate buffer (pH 8.0), 10% of glycerol (wt/v), 1% of polyvinylpyrrolidine 40,000 and 4 mM of dithiothreitol (DTT). The homogenate was centrifuged for 20 min at 48,000 g. The supernatant thus obtained was subjected to a double precipitation with ammonium sulfate at 30 and 70% of saturation. The pellet obtained from the precipitation with 70% ammonium sulfate was dissolved in a small volume of 25 mM K-phosphate buffer (pH 8.0) containing 10% of glycerol and 1 M of ammonium sulfate. The enzymatic extract was purified in 5 successive steps:

hydrophobic interaction chromatography on a column of Phenyl-Sepharose CL-4B (Pharmacia);

ionic interaction chromatography on a column of hydroxylapatite (Econo-Pac HTP, BioRad);

molecular exclusion chromatography on a column of Superose 12 HR of type FPLC (Pharmacia);

ion exchange chromatography on a MonoQ 5/5 column of FPLC type (Pharmacia);

chromatography by denaturing electrophoresis (SDS-PAGE).

The protein thus purified to homogeneity by SDS-PAGE was hydrolysed overnight at 30° C. by a lysine endoprotease and the peptides released were separated by HPLC on a reverse phase DEAE-C18 column. Five of the separated peptides were sequenced with the aid of an Applied Biosystems 470 microsequencer.

Isolation and nucleotide sequence of the VRER gene

With the aid of degenerate primers derived from these peptide sequences, a DNA fragment was amplified by the PCR procedure ("polymerase chain reaction"). A reverse PCR then made it possible to isolate the 3' and 5' parts of this clone. Finally, the full length clone was then isolated by choosing the primers suitable for the 3' and 5' ends and was sequenced several times. The complementary DNA possesses an open reading frame of 975 nucleotides. The amino acid sequence deduced indicates that the clone codes for a polypeptide composed of 325 amino acids. The size of the protein is estimated at 36 kD and has an expected pI of 6.34. The sequence of the VRER gene exhibits homologies (between 20 and 26% of identity at the amino acid level) with the proteins of the family of the dihydroflavonol reductases, and with the HC toxin of maize.

In order to verify that the protein encoded in this gene exhibits a "eutypine reductase" activity and is capable of reducing eutypine, this protein was overexpressed in a bacterial system, *Escherichia coli,* which is incapable of reducing eutypine in the natural state. For that, the complementary DNA of the VRER gene was cloned in an expression vector, then transferred into the bacteria. The lysate of these bacteria which overexpress the protein corresponding to the VRER gene uses the co-factor NADPH to reduce eutypine. The production of eutypinol was demonstrated by thin layer chromatography of a bacterial lysate incubated in the presence of radioactive eutypine. All of these data show that the protein corresponding to the VRER gene exhibits a "eutypine reductase" activity in vitro.

Biochemical characteristics of the protein encoded in the VRER gene.

The protein encoded in the VRER gene was characterized biochemically. It has a Km of 16.4 M for eutypine, which represents an excellent affinity of this enzyme for the substrate eutypine. It was also investigated whether this protein was capable of reducing other substrates. The family of the benzaldehydes (benzaldehyde and some of its derivatives such as methylbenzaldehyde, methoxybenzaldehyde, nitrobenzaldehyde, fluorobenzaldehyde possessing a group in the meta and para position), linear aldehydes such as decylaldehyde or hexanal, or other cyclic compounds possessing an aldehyde function like 4-pyridine carbaldehyde or 2-fluoraldehyde are also reduced by the ER protein in the presence of NADPH.

III—Study of the expression of the VRER gene in grapevine cells The objective of this study was to verify whether the expression of the VRER gene in grapevine cells is capable of increasing their capacity to metabolize eutypine to eutypinol. For that, the VRER gene was introduced into a binary transformation vector, then integrated into the calluses of the grapevine cv Gamay. The transformed calluses were then confronted with eutypine in order to analyze their behaviour and to determine the level of resistance of the plant to eutypine.

Integration of the VRER gene in a binary transformation vector

The VRER gene was integrated into the binary plasmid pGA (An G et al., Binary vectors. In Plant Molecular Biology Manual A3. Kluwer Acad. Pub., Dordrecht, The Nederlands, 1–19) between the right (RB) and the left (LB) borders. This binary vector contains the genes for resistance to kanamycin and tetracycline. The gene of interest was cloned into the T-DNA, behind the 35S promoter of the CaMV which enables it to be expressed in plant cells.

The schematic representation of the binary vector pGA-ER thus obtained is given in FIG. 2.

The plasmid pGA-ER was introduced into *Agrobacterium tumefaciens* strain C58. The presence of this plasmid in the bacteria transformed on selective medium (kanamycin 10 mg/l and tetracycline 5 mg/l) was confirmed by PCR analysis. The C58 strain of *Agrobacterium tumefaciens* containing the plasmid pGA-ER is then designated AbC58-ER. It will be used subsequently to carry out transformation experiments on calluses of *Vitis vinifera* cv Gamay.

Transformation of the grapevine calluses via *Agrobacterium tumefaciens*

The transformation experiments were carried out on calluses of *Vitis vinifera* cv Gamay, obtained from epiderman cells of the fruit.

The genetic transformation of the calluses of *Vitis vinifera* cv Gamay was carried out via the *Agrobacterium tumefaciens* strain AbC58-ER, containing the binary vector pAG-ER.

The calluses, cultured for 8 days in a 55 mm Petri dish (10 calluses per dish), were immersed in the bacterial suspension for 20 minutes. The inoculum was then removed by aspiration and the calluses were dried for 5 minutes in the hood. They were then transferred to a new medium, on the top of which a paper disk was placed, and cultured in the dark at a temperature of 28° C. At the end of a o-culture for 48 hours, the calluses were rinsed carefully with culture medium containing 400 mg/l of carbenicillin (antibiotic intended to eliminate the bacteria), dried on blotting paper and transferred to a new medium with 400 mg/l of carbenicillin. The selection pressure was applied 7 days after inoculation: the calluses were transferred to a selective "Gamay" medium containing a selective antibiotic (kanamycin at 75 mg/l), in addition to carbenicillin.

The calluses were maintained on the "Gamay" medium, subcultured every 20 days on fresh selective medium and placed in a culture chamber at 24° C., with an illumination of 100 $\mu$mol.m$^{-2}$. sec$^{-1}$ and a photoperiod of 16 hours.

Three months later, after 4 successive subcultures on selective new medium, calluses tolerant to kanamycin were obtained. They were then maintained on selective culture media containing 75 mg/l of kanamycin.

The verification of the integration of the VRER gene in the genome of the grapevine calluses expressing marked resistance to kanamycin was performed by the PCR (polymerase chain reaction) method and by molecular hybridization (Southern blot). Finally, the level of expression of the transgene was determined by Western blot, with the aid of antibodies directed against the ER protein.

Analysis of the behaviour of transformed grapevine calluses towards eutypine

The genetically transformed grapevine calluses and expressing the VRER transgene have then been confronted with eutypine to determine the level of resistance acquired by these tissues to eutypine.

Two biotests were used. The first (biotest I) is based on the confrontation of grapevine cells cultured in suspension with eutypine applied at different concentrations. The second makes use of grapevine calluses cultured on culture media containing eutypine.

In the biotest I, the percentage of dead cells was estimated by means of the erythrosine reagent. The concentration of eutypine inducing a percentage of dead cells of 50% is determined in the wildtype strain and in the transformed varieties. The results presented in Table III show that the cells of the transformed grapevine varieties exhibit an LD 50 2 to 2.5 times higher than that recorded for the untransformed wildtype variety.

TABLE III

Eutypine concentration causing the mortality of 50% (LD50) of the transformed (GA, GB, GC, GD) or untransformed (GWT) grapevine cells, grown in suspension in the presence of this toxic molecule.

| Cellular grapevine varieties | GWT | GA | GB | GC | GD |
|---|---|---|---|---|---|
| LD50 ($\mu$M of eutypine) | 100 | 255 | 250 | 230 | 225 |

GWT: wildtype variety, untransformed. GA, GB, GC, GD: transformed grapevine strains The biotest II reveals that the transformed grapevine calluses have acquired a level of resistance to eutypine very much greater than the capacity of the untransformed calluses. The results presented below show that the calluses of the wildtype variety do not develop in the presence of 500 $\mu$M of eutypine and necrose very rapidly. On the other hand, the GA variety, grown in the presence of eutypine supplied at a concentration which is usually lethal for these tissues, does not exhibit necroses and shows a growth practically similar to that of the control tissues which develop in the absence of eutypine (FIG. 3).

All of these results indicate that the introduction and expression of the VRER gene in the grapevine cells confer a greater resistance to this toxic molecule. It is due to the overproduction in the transformed grapevine cells of the ER protein, capable of metabolizing eutypine to eutypinol, a molecule non-toxic for the grapevine. These data show the efficacy of this gene for the detoxification of eutypine.

The transformation experiments were also performed on calluses of *Vitis vinifera* cv Ugni blanc by making use of the same experimental protocol as that used for the transformation of the calluses of *Vitis vinifera* cv. Gamay.

The analysis of the behaviour of the calluses of *Vitis vinifera* cv Ugni blanc towards eutypine was performed by using biotest II. The results presented below show that the grapevine calluses have acquired a level of resistance to eutypine very much higher than that of the untrasformed calluses. In the presence of 500 $\mu$M, the calluses of the wildtype variety necrose rapidly and do not develop. At this concentration, the growth of the calluses of the transformed UB variety is practically unaffected (Table IV). These results demonstrate the efficacy of this gene for detoxifying eutypine in the grapevine tissues.

TABLE IV

Development of the transformed (UBT) and
untransformed (UBWT) calluses of *Vitis vinifera* cv Ugni blanc
cultured in the presence of 500 µM of eutypine.

| Cell varieties | Mean mass of a callus (mg) |
|---|---|
| UBWT | 25 |
| UBT | 150 |

IV—Preparation of antibodies directed against the protein encoded in the VRER gene.

In order to obtain antibodies directed against this protein, the following procedure was used.

1.1—Cloning of the VRER gene

The cDNA fragment bearing the active part of the VRER gene was cloned into the vector pT7.7 (Tabor S et al., 1985, Proc. Natl. Acad. Sci. USA, 82, 1047–1078) at the EcoRI sites. It was then introduced in *E. coli*. After having confirmed by Southern blot that the plasmid has been correctly integrated, it was verified that the bacterial strains selected produce the ER protein capable of metabolizing eutypine into eutypinol.

1.2—Production and partial purification of the recombinant protein

The bacteria carrying the VRER transgene were placed at 42° C. for 20 minutes, then the production of the recombinant protein was allowed to proceed at 37° C. for 1 hour. After centrifugation, the bacteria were resuspended in a 0.1 M Tris HCl buffer (pH 8.0), 1 mM EDTA, 0.1 M NaCl supplemented with lysozyme (1 mg/ml). After incubation at 37° C. for 15 minutes, the solution was treated with 0.2 mg/ml of DNAse in the presence of PMSF (0.2 mM) and MgCl$_2$ (4 mM) for 15 minutes. After centrifugation at 12,000 g for 10 minutes at 4° C., the protein pellet containing the recombinant protein was washed with a 3M urea solution. After centrifugation, the protein extract was denatured in the 0.1 M Tris HCl buffer (pH 7.5) containing urea (6M). The denatured proteins were then concentrated 5 times (Centricon 10).

1.3—Immunization of rabbits by the protein extract containing the recombinant protein.

An aliquot (50 µg) of the protein extract containing the recombinant protein was fractionated by preparative electrophoresis (12% polyacrylamide gel in the presence of SDS). The proteins were then transferred to a nitrocellulose membrane and the recombinant protein was located by staining with Coomassie blue. A band of nitrocellulose bearing the recombinant protein was cut out and used as implant for the immunization of two rabbits (Eurogentec company). Four implantations were made during the first two months of immunization and the finally bleeding was done 1 month after the last immunization.

1.4—Partial purification of the antibodies directed against the ER protein.

The anti-ER protein antibodies were partially purified by exhaustion of the rabbit serum against the total proteins of *E. coli*. The proteins extracted from wildtype *E. coli* are deposited on a nitrocellulose membrane, then this latter is placed in the serum obtained from the rabbits. This operation is repeated several times until the serum is exhausted.

After verification, the serum thus obtained is used in Western blot analyses.

What is claimed is:

1. A selection marker comprising an isolated nucleotide sequence which codes for a polypeptide with eutypine reductase activity, said polypeptide comprising the following amino acid sequence SEQ ID NO:2:

```
Met Ser Thr Ala Ala Gly Lys Leu Val Cys Val Thr
Gly Ala Ser Gly Tyr Ile Ala Ser Trp Leu Val Lys
Phe Leu Leu Glu Arg Gly Tyr Thr Val Lys Ala Thr
Val Arg Asp Thr Asn Asp Pro Lys Lys Val Asp His
Leu Leu Ser Leu Asp Gly Ala Lys Glu Arg Leu His
Leu Val Lys Ala Asn Leu Leu Glu Glu Gly Ser Phe
Asp Ser Ala Val Glu Gly Val His Ala Val Phe His
Thr Ala Ser Pro Phe Phe Asn Asp Ala Lys Asp Pro
Gln Thr Glu Leu Leu Asp Pro Ala Val Lys Gly Thr
Leu Asn Val Leu Lys Ser Cys Val Asn Ser Pro Thr
Leu Lys Arg Val Val Leu Thr Ser Ser Ile Ala Ala
Val Ala Phe Ser Asp Arg Pro Lys Asn Pro Asp Val
Val Val Asp Glu Thr Trp Tyr Ser Asp Pro Glu Tyr
Cys Lys Arg Thr Gly Leu Trp Tyr Asn Leu Ser Lys
Thr Leu Ala Glu Asp Ala Ala Try Lys Phe Ala Lys
Glu Asn Asn Ile Asp Leu Val Thr Met Asn Pro Ala
Leu Val Val Gly Pro Leu Leu Gln Pro Val Leu Asn
Thr Ser Ala Ala Ile Val Leu Gly Leu Val Asn Gly
Ala Lys Thr Phe Lys Asn Ala Ser Leu Gly Trp Val
Asp Val Lys Asp Val Ala Leu Ala His Ile Leu Ala
Tyr Glu Asn Ala Ser Ala Asn Gly Arg Tyr Leu Leu
Val Glu Arg Val Ala His Phe Gly Asp Ala Ala Lys
Ile Leu Arg Asp Leu Tyr Pro Thr Leu Gln Ile Pro
Asp Lys Cys Glu Asp Asp Lys Pro Leu Glu Pro Ile
Phe Gln Val Ser Lys Glu Lys Ala Lys Ser Leu Gly
Ile Asp Tyr Ile Pro Leu Glu Val Ser Leu Lys Asp
Thr Val Glu Ser Leu Lys Glu Lys Phe Leu Lys
Val.
```

2. A recombinant nucleic acid comprising the selection marker of claim 1 and a nucleotide sequence of interest, said recombinant nucleic acid permitting the conjugate integration of the selection marker and the sequence of interest in a cell host.

3. A combination of elements consisting of i) a nucleic acid comprising the selection marker of claim 1 and ii) a nucleic acid of interest, wherein the expression of the selection marker is linked to the expression of the nucleic acid of interest when said combination is transferred into a cell host.

4. A cell host transformed with a nucleic acid comprising the selection marker of claim 1 and with a nucleotide sequence of interest, wherein the expression of the selection marker is coupled to that of the sequence of interest in the cell host.

5. A method for detecting cells transformed with a nucleotide sequence of interest comprising the steps of:

(a) transforming cells with the recombinant nucleic acid of claim 2;

(b) contacting said transformed cells with a substrate for eutypine reductase; and (c) detecting a reduction reaction undergone by the substrate, thereby detecting said cells transformed with said nucleotide sequence of interest.

6. A method for detecting cells transformed with a nucleic acid of interest comprising the steps of:

(a) transforming cells with the combination of claim 3;

(b) contacting said transformed cells with a substrate for eutypine reductase; and (c) detecting a reduction reaction undergone by the substrate, thereby detecting said cells transformed with said nucleic acid of interest.

7. The method of claim 5, further comprising the step of d) selecting said transformed cells producing said reduction reaction.

8. The method of claim 6, further comprising the step of d) selecting said transformed cells producing said reduction reaction.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 975 base pairs
        (B) TYPE: nucleic acid
        (C) STRANDEDNESS: double
        (D) TOPOLOGY: linear     (ii) MOLECULE TYPE: cDNA     (ix) FEATURE:
        (A) NAME/KEY: CDS
        (B) LOCATION: 1..975

(xi) SEQUENCE DESCRIPTION: SEQ ID NO: 1:

```
ATG AGC ACC GCC GCT GGA AAA CTA GTC TGT GTC ACC GGC GCT TCC GGT      48
Met Ser Thr Ala Ala Gly Lys Leu Val Cys Val Thr Gly Ala Ser Gly
 1               5                  10                  15

TAC ATC GCT TCC TGG CTC GTC AAG TTT CTT CTC GAA CGC GGC TAC ACC      96
Tyr Ile Ala Ser Trp Leu Val Lys Phe Leu Leu Glu Arg Gly Tyr Thr
             20                  25                  30

GTG AAG GCC ACC GTT CGC GAC ACG AAT GAT CCC AAA AAG GTA GAT CAC     144
Val Lys Ala Thr Val Arg Asp Thr Asn Asp Pro Lys Lys Val Asp His
         35                  40                  45

TTG CTC AGC CTT GAT GGT GCG AAG GAG AGA TTG CAT CTC GTG AAG GCG     192
```

```
                                                                         -continued Leu Leu Ser Leu Asp Gly Ala Lys Glu Arg Leu His Leu Val Lys Ala
    50                  55                  60

AAT CTT CTA GAA GAA GGT TCC TTT GAC TCT GCC GTT GAA GGT GTT CAC        240
Asn Leu Leu Glu Glu Gly Ser Phe Asp Ser Ala Val Glu Gly Val His
65                  70                  75                  80

GCT GTG TTT CAC ACT GCT TCT CCC TTT TTC AAC GAT GCC AAA GAT CCG        288
Ala Val Phe His Thr Ala Ser Pro Phe Phe Asn Asp Ala Lys Asp Pro
                85                  90                  95

CAG ACT GAG TTG TTG GAC CCG GCA GTG AAG GGG ACT CTG AAT GTT CTG        336
Gln Thr Glu Leu Leu Asp Pro Ala Val Lys Gly Thr Leu Asn Val Leu
            100                 105                 110

AAA TCG TGT GTG AAC TCG CCC ACG CTG AAA CGC GTC GTT TTA ACT TCT        384
Lys Ser Cys Val Asn Ser Pro Thr Leu Lys Arg Val Val Leu Thr Ser
        115                 120                 125

TCT ATT GCT GCA GTT GCG TTC AGC GAC AGG CCT AAA AAC CCT GAT GTT        432
Ser Ile Ala Ala Val Ala Phe Ser Asp Arg Pro Lys Asn Pro Asp Val
    130                 135                 140

GTG GTT GAC GAG ACT TGG TAT TCT GAC CCG GAA TAC TGT AAG AGA ACA        480
Val Val Asp Glu Thr Trp Tyr Ser Asp Pro Glu Tyr Cys Lys Arg Thr
145                 150                 155                 160

GGG TTA TGG TAT AAC CTT TCA AAG ACT CTG GCC GAA GAT GCT GCC TGG        528
Gly Leu Trp Tyr Asn Leu Ser Lys Thr Leu Ala Glu Asp Ala Ala Trp
                165                 170                 175

AAA TTT GCG AAA GAA AAC AAC ATT GAC CTG GTT ACA ATG AAC CCA GCA        576
Lys Phe Ala Lys Glu Asn Asn Ile Asp Leu Val Thr Met Asn Pro Ala
            180                 185                 190

TTG GTT GTT GGA CCT CTC TTG CAA CCA GTG CTT AAT ACT AGC GCT GCT        624
Leu Val Val Gly Pro Leu Leu Gln Pro Val Leu Asn Thr Ser Ala Ala
        195                 200                 205

ATA GTT TTA GGT TTA GTT AAT GGG GCG AAA ACA TTT AAA AAT GCT TCT        672
Ile Val Leu Gly Leu Val Asn Gly Ala Lys Thr Phe Lys Asn Ala Ser
    210                 215                 220

TTG GGA TGG GTC GAC GTG AAA GAT GTT GCA TTG GCC CAT ATT CTA GCA        720
Leu Gly Trp Val Asp Val Lys Asp Val Ala Leu Ala His Ile Leu Ala
225                 230                 235                 240

TAT GAG AAT GCT TCG GCT AAT GGA AGA TAT TTA CTA GTT GAG AGA GTA        768
Tyr Glu Asn Ala Ser Ala Asn Gly Arg Tyr Leu Leu Val Glu Arg Val
                245                 250                 255

GCA CAC TTT GGA GAT GCT GCC AAG ATT TTA CGA GAT TTA TAC CCA ACA        816
Ala His Phe Gly Asp Ala Ala Lys Ile Leu Arg Asp Leu Tyr Pro Thr
            260                 265                 270

TTG CAA ATT CCA GAC AAG TGT GAA GAC GAT AAG CCA TTA GAA CCA ATA        864
Leu Gln Ile Pro Asp Lys Cys Glu Asp Asp Lys Pro Leu Glu Pro Ile
        275                 280                 285

TTT CAG GTT TCG AAG GAA AAA GCA AAG AGC TTG GGG ATT GAC TAT ATT        912
Phe Gln Val Ser Lys Glu Lys Ala Lys Ser Leu Gly Ile Asp Tyr Ile
    290                 295                 300

CCT TTG GAA GTG AGC CTC AAG GAC ACT GTG GAG AGC TTG AAG GAA AAG        960
Pro Leu Glu Val Ser Leu Lys Asp Thr Val Glu Ser Leu Lys Glu Lys
305                 310                 315                 320

AAG TTT CTG AAA GTT                                                    975
Lys Phe Leu Lys Val
                325

(2) INFORMATION FOR SEQ ID NO: 2:

(i) SEQUENCE CHARACTERISTICS:
        (A) LENGTH: 325 amino acids
        (B) TYPE: amino acid
        (D) TOPOLOGY: linear
```

(ii) MOLECULE TYPE: protein (xi) SEQUENCE DESCRIPTION: SEQ ID NO: 2:

```
Met Ser Thr Ala Ala Gly Lys Leu Val Cys Val Thr Gly Ala Ser Gly
 1               5                  10                  15

Tyr Ile Ala Ser Trp Leu Val Lys Phe Leu Leu Glu Arg Gly Tyr Thr
                20                  25                  30

Val Lys Ala Thr Val Arg Asp Thr Asn Asp Pro Lys Lys Val Asp His
             35                  40                  45

Leu Leu Ser Leu Asp Gly Ala Lys Glu Arg Leu His Leu Val Lys Ala
     50                  55                  60

Asn Leu Leu Glu Glu Gly Ser Phe Asp Ser Ala Val Glu Gly Val His
 65                  70                  75                  80

Ala Val Phe His Thr Ala Ser Pro Phe Phe Asn Asp Ala Lys Asp Pro
                 85                  90                  95

Gln Thr Glu Leu Leu Asp Pro Ala Val Lys Gly Thr Leu Asn Val Leu
                100                 105                 110

Lys Ser Cys Val Asn Ser Pro Thr Leu Lys Arg Val Val Leu Thr Ser
                115                 120                 125

Ser Ile Ala Ala Val Ala Phe Ser Asp Arg Pro Lys Asn Pro Asp Val
    130                 135                 140

Val Val Asp Glu Thr Trp Tyr Ser Asp Pro Glu Tyr Cys Lys Arg Thr
145                 150                 155                 160

Gly Leu Trp Tyr Asn Leu Ser Lys Thr Leu Ala Glu Asp Ala Ala Trp
                    165                 170                 175

Lys Phe Ala Lys Glu Asn Asn Ile Asp Leu Val Thr Met Asn Pro Ala
                180                 185                 190

Leu Val Val Gly Pro Leu Leu Gln Pro Val Leu Asn Thr Ser Ala Ala
                195                 200                 205

Ile Val Leu Gly Leu Val Asn Gly Ala Lys Thr Phe Lys Asn Ala Ser
    210                 215                 220

Leu Gly Trp Val Asp Val Lys Asp Val Ala Leu Ala His Ile Leu Ala
225                 230                 235                 240

Tyr Glu Asn Ala Ser Ala Asn Gly Arg Tyr Leu Leu Val Glu Arg Val
                245                 250                 255

Ala His Phe Gly Asp Ala Ala Lys Ile Leu Arg Asp Leu Tyr Pro Thr
                260                 265                 270

Leu Gln Ile Pro Asp Lys Cys Glu Asp Lys Pro Leu Glu Pro Ile
                275                 280                 285

Phe Gln Val Ser Lys Glu Lys Ala Lys Ser Leu Gly Ile Asp Tyr Ile
                290                 295                 300

Pro Leu Glu Val Ser Leu Lys Asp Thr Val Glu Ser Leu Lys Glu Lys
305                 310                 315                 320

Lys Phe Leu Lys Val
                325
```

(2) INFORMATION FOR SEQ ID NO: 3:

(i) SEQUENCE CHARACTERISTICS:
        (A) LENGTH: 1254 base pairs
        (B) TYPE: nucleic acid
        (C) STRANDEDNESS: double
        (D) TOPOLOGY: linear     (ii) MOLECULE TYPE: cDNA     (ix) FEATURE:

(A) NAME/KEY: CDS
(B) LOCATION: 22..996

(xi) SEQUENCE DESCRIPTION: SEQ ID NO: 3:

| | | | | | | | | | | | | | | | | |
|---|---|---|---|---|---|---|---|---|---|---|---|---|---|---|---|---|
| GCAGAATCAA | CATAATCCAC | A | ATG | AGC | ACC | GCC | GCT | GGA | AAA | CTA | GTC | TGT | | | | 51 |
| | | | Met | Ser | Thr | Ala | Ala | Gly | Lys | Leu | Val | Cys | | | | |
| | | | 1 | | | | 5 | | | | | 10 | | | | |

| GTC | ACC | GGC | GCT | TCC | GGT | TAC | ATC | GCT | TCC | TGG | CTC | GTC | AAG | TTT | CTT | 99 |
|---|---|---|---|---|---|---|---|---|---|---|---|---|---|---|---|---|
| Val | Thr | Gly | Ala | Ser | Gly | Tyr | Ile | Ala | Ser | Trp | Leu | Val | Lys | Phe | Leu | |
| | | | | 15 | | | | | 20 | | | | | 25 | | |

| CTC | GAA | CGC | GGC | TAC | ACC | GTG | AAG | GCC | ACC | GTT | CGC | GAC | ACG | AAT | GAT | 147 |
|---|---|---|---|---|---|---|---|---|---|---|---|---|---|---|---|---|
| Leu | Glu | Arg | Gly | Tyr | Thr | Val | Lys | Ala | Thr | Val | Arg | Asp | Thr | Asn | Asp | |
| | | | 30 | | | | | 35 | | | | | 40 | | | |

| CCC | AAA | AAG | GTA | GAT | CAC | TTG | CTC | AGC | CTT | GAT | GGT | GCG | AAG | GAG | AGA | 195 |
|---|---|---|---|---|---|---|---|---|---|---|---|---|---|---|---|---|
| Pro | Lys | Lys | Val | Asp | His | Leu | Leu | Ser | Leu | Asp | Gly | Ala | Lys | Glu | Arg | |
| | | | 45 | | | | | 50 | | | | | 55 | | | |

| TTG | CAT | CTC | GTG | AAG | GCG | AAT | CTT | CTA | GAA | GAA | GGT | TCC | TTT | GAC | TCT | 243 |
|---|---|---|---|---|---|---|---|---|---|---|---|---|---|---|---|---|
| Leu | His | Leu | Val | Lys | Ala | Asn | Leu | Leu | Glu | Glu | Gly | Ser | Phe | Asp | Ser | |
| | 60 | | | | | 65 | | | | | 70 | | | | | |

| GCC | GTT | GAA | GGT | GTT | CAC | GCT | GTG | TTT | CAC | ACT | GCT | TCT | CCC | TTT | TTC | 291 |
|---|---|---|---|---|---|---|---|---|---|---|---|---|---|---|---|---|
| Ala | Val | Glu | Gly | Val | His | Ala | Val | Phe | His | Thr | Ala | Ser | Pro | Phe | Phe | |
| 75 | | | | | 80 | | | | | 85 | | | | | 90 | |

| AAC | GAT | GCC | AAA | GAT | CCG | CAG | ACT | GAG | TTG | TTG | GAC | CCG | GCA | GTG | AAG | 339 |
|---|---|---|---|---|---|---|---|---|---|---|---|---|---|---|---|---|
| Asn | Asp | Ala | Lys | Asp | Pro | Gln | Thr | Glu | Leu | Leu | Asp | Pro | Ala | Val | Lys | |
| | | | | 95 | | | | | 100 | | | | | 105 | | |

| GGG | ACT | CTG | AAT | GTT | CTG | AAA | TCG | TGT | GTG | AAC | TCG | CCC | ACG | CTG | AAA | 387 |
|---|---|---|---|---|---|---|---|---|---|---|---|---|---|---|---|---|
| Gly | Thr | Leu | Asn | Val | Leu | Lys | Ser | Cys | Val | Asn | Ser | Pro | Thr | Leu | Lys | |
| | | | 110 | | | | | 115 | | | | | 120 | | | |

| CGC | GTC | GTT | TTA | ACT | TCT | TCT | ATT | GCT | GCA | GTT | GCG | TTC | AGC | GAC | AGG | 435 |
|---|---|---|---|---|---|---|---|---|---|---|---|---|---|---|---|---|
| Arg | Val | Val | Leu | Thr | Ser | Ser | Ile | Ala | Ala | Val | Ala | Phe | Ser | Asp | Arg | |
| | | 125 | | | | | 130 | | | | | 135 | | | | |

| CCT | AAA | AAC | CCT | GAT | GTT | GTG | GTT | GAC | GAG | ACT | TGG | TAT | TCT | GAC | CCG | 483 |
|---|---|---|---|---|---|---|---|---|---|---|---|---|---|---|---|---|
| Pro | Lys | Asn | Pro | Asp | Val | Val | Val | Asp | Glu | Thr | Trp | Tyr | Ser | Asp | Pro | |
| 140 | | | | | 145 | | | | | 150 | | | | | | |

| GAA | TAC | TGT | AAG | AGA | ACA | GGG | TTA | TGG | TAT | AAC | CTT | TCA | AAG | ACT | CTG | 531 |
|---|---|---|---|---|---|---|---|---|---|---|---|---|---|---|---|---|
| Glu | Tyr | Cys | Lys | Arg | Thr | Gly | Leu | Trp | Tyr | Asn | Leu | Ser | Lys | Thr | Leu | |
| 155 | | | | | 160 | | | | | 165 | | | | | 170 | |

| GCC | GAA | GAT | GCT | GCC | TGG | AAA | TTT | GCG | AAA | GAA | AAC | AAC | ATT | GAC | CTG | 579 |
|---|---|---|---|---|---|---|---|---|---|---|---|---|---|---|---|---|
| Ala | Glu | Asp | Ala | Ala | Trp | Lys | Phe | Ala | Lys | Glu | Asn | Asn | Ile | Asp | Leu | |
| | | | 175 | | | | | 180 | | | | | 185 | | | |

| GTT | ACA | ATG | AAC | CCA | GCA | TTG | GTT | GTT | GGA | CCT | CTC | TTG | CAA | CCA | GTG | 627 |
|---|---|---|---|---|---|---|---|---|---|---|---|---|---|---|---|---|
| Val | Thr | Met | Asn | Pro | Ala | Leu | Val | Val | Gly | Pro | Leu | Leu | Gln | Pro | Val | |
| | | | 190 | | | | | 195 | | | | | 200 | | | |

| CTT | AAT | ACT | AGC | GCT | GCT | ATA | GTT | TTA | GGT | TTA | GTT | AAT | GGG | GCG | AAA | 675 |
|---|---|---|---|---|---|---|---|---|---|---|---|---|---|---|---|---|
| Leu | Asn | Thr | Ser | Ala | Ala | Ile | Val | Leu | Gly | Leu | Val | Asn | Gly | Ala | Lys | |
| | | 205 | | | | | 210 | | | | | 215 | | | | |

| ACA | TTT | AAA | AAT | GCT | TCT | TTG | GGA | TGG | GTC | GAC | GTG | AAA | GAT | GTT | GCA | 723 |
|---|---|---|---|---|---|---|---|---|---|---|---|---|---|---|---|---|
| Thr | Phe | Lys | Asn | Ala | Ser | Leu | Gly | Trp | Val | Asp | Val | Lys | Asp | Val | Ala | |
| 220 | | | | | 225 | | | | | 230 | | | | | | |

| TTG | GCC | CAT | ATT | CTA | GCA | TAT | GAG | AAT | GCT | TCG | GCT | AAT | GGA | AGA | TAT | 771 |
|---|---|---|---|---|---|---|---|---|---|---|---|---|---|---|---|---|
| Leu | Ala | His | Ile | Leu | Ala | Tyr | Glu | Asn | Ala | Ser | Ala | Asn | Gly | Arg | Tyr | |
| 235 | | | | 240 | | | | | 245 | | | | | 250 | | |

| TTA | CTA | GTT | GAG | AGA | GTA | GCA | CAC | TTT | GGA | GAT | GCT | GCC | AAG | ATT | TTA | 819 |
|---|---|---|---|---|---|---|---|---|---|---|---|---|---|---|---|---|
| Leu | Leu | Val | Glu | Arg | Val | Ala | His | Phe | Gly | Asp | Ala | Ala | Lys | Ile | Leu | |
| | | | | 255 | | | | | 260 | | | | | 265 | | |

| CGA | GAT | TTA | TAC | CCA | ACA | TTG | CAA | ATT | CCA | GAC | AAG | TGT | GAA | GAC | GAT | 867 |
|---|---|---|---|---|---|---|---|---|---|---|---|---|---|---|---|---|
| Arg | Asp | Leu | Tyr | Pro | Thr | Leu | Gln | Ile | Pro | Asp | Lys | Cys | Glu | Asp | Asp | |
| | | 270 | | | | | 275 | | | | | 280 | | | | |

| AAG | CCA | TTA | GAA | CCA | ATA | TTT | CAG | GTT | TCG | AAG | GAA | AAA | GCA | AAG | AGC | 915 |
|---|---|---|---|---|---|---|---|---|---|---|---|---|---|---|---|---|
| Lys | Pro | Leu | Glu | Pro | Ile | Phe | Gln | Val | Ser | Lys | Glu | Lys | Ala | Lys | Ser | |

```
                    285                 290                 295
TTG GGG ATT GAC TAT ATT CCT TTG GAA GTG AGC CTC AAG GAC ACT GTG    963
Leu Gly Ile Asp Tyr Ile Pro Leu Glu Val Ser Leu Lys Asp Thr Val
    300                 305                 310

GAG AGC TTG AAG GAA AAG AAG TTT CTG AAA GTT TAATGTTACC CTTCAAGA   1016
Glu Ser Leu Lys Glu Lys Lys Phe Leu Lys Val
315                 320                 325

CGTGGAAACC TTCTTATGCC TATGCTTGAG GTAAACTTAG TGTTAAATAA ATGGAAAG   1076

ATGTAAGTTC TGTAATAAGT GATTCTTGGA CTGGTTTTTT CTGGTGACAA GTTTCAAA   1136

TGAGTGACCA TGGTAGAGTC TGCGTTCCAG ATTGTATCCT TGTGATATTG TATTAGTA   1196

AGATGTTTGT TGCAGCTAAT GCACCCATTA TTATGTTTTT ATCAAAAAAA AAAAAAAA   1254

(2) INFORMATION FOR SEQ ID NO: 4:

(i) SEQUENCE CHARACTERISTICS:
        (A) LENGTH: 325 amino acids
        (B) TYPE: amino acid
        (D) TOPOLOGY: linear (ii) MOLECULE TYPE: protein (xi) SEQUENCE DESCRIPTION: SEQ ID NO: 4:

Met Ser Thr Ala Ala Gly Lys Leu Val Cys Val Thr Gly Ala Ser Gly
1               5                   10                  15

Tyr Ile Ala Ser Trp Leu Val Lys Phe Leu Leu Glu Arg Gly Tyr Thr
                20                  25                  30

Val Lys Ala Thr Val Arg Asp Thr Asn Asp Pro Lys Lys Val Asp His
            35                  40                  45

Leu Leu Ser Leu Asp Gly Ala Lys Glu Arg Leu His Leu Val Lys Ala
    50                  55                  60

Asn Leu Glu Glu Gly Ser Phe Asp Ser Ala Val Glu Gly Val His
65              70                  75                  80

Ala Val Phe His Thr Ala Ser Pro Phe Phe Asn Asp Ala Lys Asp Pro
                85                  90                  95

Gln Thr Glu Leu Leu Asp Pro Ala Val Lys Gly Thr Leu Asn Val Leu
            100                 105                 110

Lys Ser Cys Val Asn Ser Pro Thr Leu Lys Arg Val Val Leu Thr Ser
        115                 120                 125

Ser Ile Ala Ala Val Ala Phe Ser Asp Arg Pro Lys Asn Pro Asp Val
    130                 135                 140

Val Val Asp Glu Thr Trp Tyr Ser Asp Pro Glu Tyr Cys Lys Arg Thr
145                 150                 155                 160

Gly Leu Trp Tyr Asn Leu Ser Lys Thr Leu Ala Glu Asp Ala Ala Trp
                165                 170                 175

Lys Phe Ala Lys Glu Asn Asn Ile Asp Leu Val Thr Met Asn Pro Ala
            180                 185                 190

Leu Val Val Gly Pro Leu Leu Gln Pro Val Leu Asn Thr Ser Ala Ala
        195                 200                 205

Ile Val Leu Gly Leu Val Asn Gly Ala Lys Thr Phe Lys Asn Ala Ser
    210                 215                 220

Leu Gly Trp Val Asp Val Lys Asp Val Ala Leu Ala His Ile Leu Ala
225                 230                 235                 240

Tyr Glu Asn Ala Ser Ala Asn Gly Arg Tyr Leu Leu Val Glu Arg Val
                245                 250                 255

Ala His Phe Gly Asp Ala Ala Lys Ile Leu Arg Asp Leu Tyr Pro Thr
```

-continued

```
                260               265               270
Leu Gln Ile Pro Asp Lys Cys Glu Asp Asp Lys Pro Leu Glu Pro Ile
        275                   280                   285
Phe Gln Val Ser Lys Glu Lys Ala Lys Ser Leu Gly Ile Asp Tyr Ile
    290                   295                   300
Pro Leu Glu Val Ser Leu Lys Asp Thr Val Glu Ser Leu Lys Glu Lys
305                   310                   315                   320
Lys Phe Leu Lys Val
                325
```